United States Patent
Chauhan et al.

(10) Patent No.: US 9,011,904 B2
(45) Date of Patent: Apr. 21, 2015

(54) SELF-BREAKING TABLETS

(75) Inventors: Ishwar Chauhan, Voorhees, NJ (US); Siva Rama Krishna Nutalapati, Princeton, NJ (US)

(73) Assignee: Aptapharma, Inc., Pennsauken, NJ (US)

( * ) Notice: Subject to any disclaimer, the term of this patent is extended or adjusted under 35 U.S.C. 154(b) by 101 days.

(21) Appl. No.: 13/380,943

(22) PCT Filed: Jul. 2, 2010

(86) PCT No.: PCT/US2010/040911
§ 371 (c)(1),
(2), (4) Date: Feb. 9, 2012

(87) PCT Pub. No.: WO2011/005686
PCT Pub. Date: Jan. 13, 2011

(65) Prior Publication Data
US 2012/0128766 A1      May 24, 2012

Related U.S. Application Data

(60) Provisional application No. 61/223,289, filed on Jul. 6, 2009.

(51) Int. Cl.
A61K 9/20 (2006.01)
A61K 9/28 (2006.01)

(52) U.S. Cl.
CPC ............. *A61K 9/2072* (2013.01); *A61K 9/2846* (2013.01); *A61K 9/2866* (2013.01); *A61K 9/2886* (2013.01)

(58) Field of Classification Search
CPC . A61K 9/2072; A61K 9/2846; A61K 9/2866; A61K 9/2886
See application file for complete search history.

(56) References Cited

U.S. PATENT DOCUMENTS

| | | | |
|---|---|---|---|
| 6,602,521 B1 | 8/2003 | Ting et al. | 424/471 |
| 2006/0257482 A1 | 11/2006 | Kumar et al. | 424/469 |
| 2007/0031488 A1 | 2/2007 | Solomon et al. | 424/464 |
| 2008/0260824 A1 | 10/2008 | Nangia et al. | 424/468 |

OTHER PUBLICATIONS

Yoshioka et al. (Stability of Drugs and Dosage Forms 2000; Springer. 268 pages; 4 pages).*
Crowley (Drug-Excipient Interactions Pharmaceutical Technology Europe. 2001; 6 pages).*
Noviasky et al. "Clinical Inquiries. Which Medications Can Be Split without Compromising Efficacy and Safety?" The Journal of Family Practice 2006 55(8):707-708.

* cited by examiner

*Primary Examiner* — Ernst V Arnold
(74) *Attorney, Agent, or Firm* — Licata & Tyrrell P.C.

(57) ABSTRACT

Self-breaking core tablets and functionally coated tablets and capsule formulations are provided. Methods for production of these tablet and capsule formulations and their administration are also provided.

11 Claims, 3 Drawing Sheets

SELF-BREAKING TABLETS

This patent application is the U.S. National Stage Application of International Application No. PCT/US2010/0040911 filed Jul. 2, 2010, which claims the benefit of priority from U.S. Provisional Application Ser. No. 61/223,289, filed Jul. 6, 2009, teachings of each of which are herein incorporated by reference in their entirety.

FIELD OF THE INVENTION

The present invention provides self-breaking oral tablet and capsule formulations.

BACKGROUND OF THE INVENTION

For many tablets, particularly coated controlled, modified or delayed release prescription medication tablets, the drug release profile is altered or compromised upon breaking or splitting. Generally, single unit coated tablets cannot be broken into small pieces without compromising the coating. Such compromises result in differences in drug release profile rendering breaking or sprinkling of the tablet or capsule unacceptable. Thus, the American Medical Society and American Pharmacists Association recommends against splitting tablets that are modified release, combination products, unscored, film coated, friable or dose critical (Noviasky et al. The Journal of Family Practice, jfponline with the extension .com/Pages.asp?AID=4326 of the World Wide Web).

Many orally administered tablet preparations are coated either to achieve specific release profile or due to the rapid degradation of the drug in the acidic conditions of the stomach. Enteric protection is most commonly used to safeguard the drug from the acidic conditions of the stomach and is achieved by formulating enteric-coated granules within capsules, enteric-coated tablets, and enteric-coated multiple-unit pellet system commonly referred to as MUPS compressed into tablets.

For example, Omeprazole magnesium tablets manufactured by AstraZeneca (Prilosec OTC) are formulated as a "multiple unit pellet system" (MUPS). Essentially, the tablet consists of extremely small enteric-coated granules (pellets) of Omeprazole magnesium compressed into tablets using acceptable pharmaceutical excipients.

Information from clinical trials in patients with duodenal ulcers in remission indicates that the enteric coated Omeprazole magnesium 20 mg tablets (as a single unit formulation) and Omeprazole magnesium 20 mg capsules (as a multiple unit formulation) are not bioequivalent in terms of plasma AUC, $C_{max}$ and $t_{max}$. The enteric coated Omeprazole magnesium 20 mg tablets demonstrate, after repeated dosing, increased plasma Omeprazole AUC (18%) and maximum concentration (41%) in comparison to Omeprazole magnesium 20 mg given as capsules (as a multiple unit formulation).

Such differences in the pharmacokinetic parameters make substituting multiple unit pellet formulations of a drug with a single unit tablet formulation of the same drug extremely difficult.

SUMMARY OF THE INVENTION

The present invention relates to self-breaking tablet and capsule formulations which exhibit pharmacokinetic parameters closer to multiparticulate formulations than single unit tablet formulations. These formulations also provide a means for efficiently and effectively administering to a drug orally to patients who cannot swallow an entire tablet or capsule.

In one embodiment, the formulation is a functionally coated tablet comprising two or more drug containing units separated by a self-breaking layer or layers. In this embodiment, the self-breaking layer or layers may comprise one or more drugs to function as an immediate release drug containing unit. Alternatively, or in addition, the self-breaking layer may comprise agents that improve patient compliance such as flavors, sweeteners, effervescent agents, coloring agents and such.

In another embodiment, the formulation is a functionally coated tablet comprising two or more drug containing units, a plug adjacent to each drug containing unit, one or more self-breaking layers positioned between plugs of the tablet. Upon contact with an aqueous media, the self-breaking layer disintegrates, thereby breaking the tablet into the two or more functionally coated drug containing units with plugs. The plugs prevent compromise and/or differences in drug release profile of the drug containing units caused by breakage and/or disintegration of the self-breaking layer of the tablet. In this embodiment, the self-breaking layer or layers may comprise one or more drugs and function as an immediate release drug containing unit. Alternatively, or in addition, the self-breaking layer or layers may comprise agents that improve patient compliance such as flavors, sweeteners, effervescent agents, coloring agents and such.

In one embodiment, the tablet further comprises a subcoating.

In one embodiment, one or more of the functionally coated tablets or core tablets comprising two or more drug containing units separated by a self-breaking layer or two or more drug containing units separated by plugs and a self-breaking layer are encapsulated in a capsule.

Another aspect of the present invention relates to a method for producing functionally coated self-breaking tablets or capsules thereof.

In one embodiment, a self-breaking tablet of the present invention is produced by compressing into a tablet a first drug containing unit, a self-breaking layer, and a second drug containing unit into a tablet and coating the tablet with a functional coating or film. In this embodiment, the self-breaking layer may comprise one or more drugs to function as an immediate release drug containing unit. Alternatively, or in addition, the self-breaking layer may comprise agents that improve patient compliance.

In another embodiment, a self-breaking tablet of the present invention is produced by compressing into a tablet a first drug containing unit, a first plug, a self-breaking layer or unit, a second plug and a second drug containing unit and coating the tablet with a functional coating or film. In this embodiment, the self-breaking layer may comprise one or more drugs to function as an immediate release drug containing unit. Alternatively, or in addition, the self-breaking layer may comprise agents that improve patient compliance.

In one embodiment, the method further comprises coating the tablet with a subcoating prior to coating with a functional coating or film.

Functionally coated tablets of the present invention as well as core tablets comprising two or more drug containing units separated by a self-breaking layer or two or more drug containing units separated by plugs and a self-breaking layer may be encapsulated in a capsule for capsule formulations.

Another aspect of the present invention relates to methods for orally administering a modified release drug to a subject via these formulations.

Yet another aspect of the present invention relates to methods for administering a modified release drug and an immediate release drug via these formulations.

DETAILED DESCRIPTION OF THE INVENTION

The present invention provides new formulations for orally administered functionally coated tablets and capsules of functionally coated tablets or core tablets thereof. The self-breaking tablet and capsule formulations of the present invention exhibit pharmacokinetic parameters closer to multiparticulate formulations than single unit tablet formulations.

Formulations of the present invention can be used with any orally administered drug which can be compressed into tablet layers.

Various embodiments of core tablets and coated tablets of the present invention are depicted in FIGS. 1 through 4.

Figure 1:
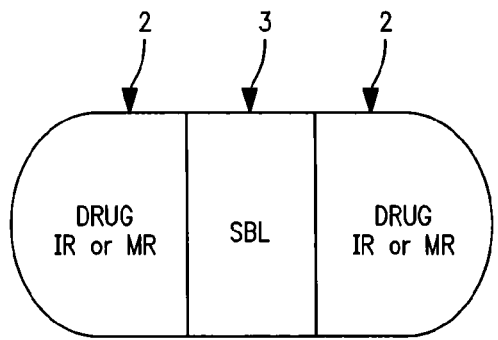
FIG. 1 is a diagram depicting a core tablet with two drug containing units (Drug) separated by a self-breaking layer (SBL).
Figure 2:
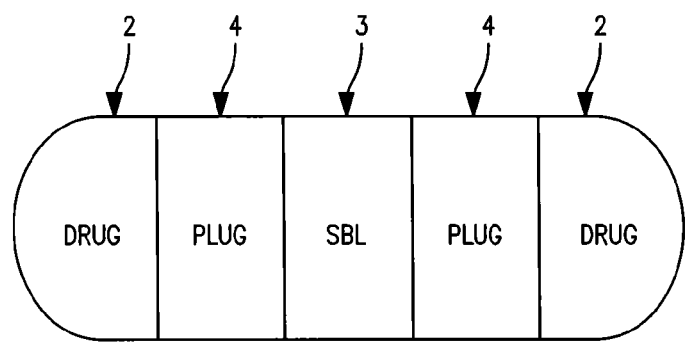
FIG. 2 is a diagram depicting a core tablet with two drug containing units (Drug) with plugs (Plug) separated by a self-breaking layer (SBL).
Figure 3:
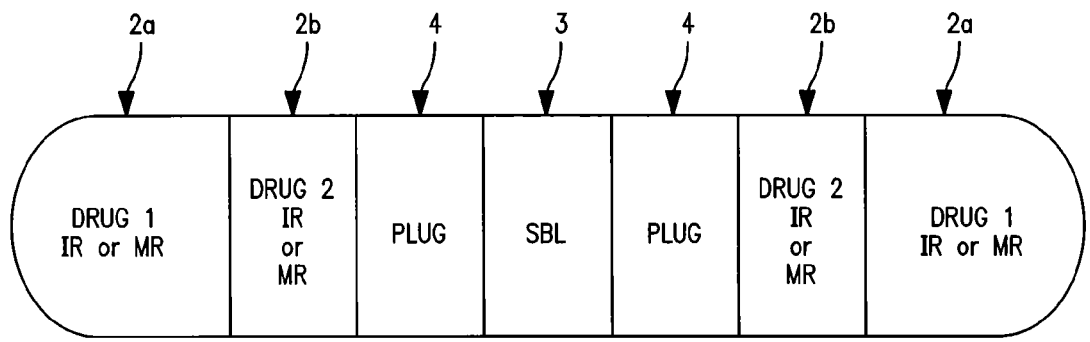
FIG. 3 is a diagram depicting a core tablet with drug containing units with multiple drug containing layers and multiple drug release layers. The multiple drug containing layers of each drug containing unit are designated as "Drug 1" and "Drug 2". The multiple drug release layers of each drug containing unit are designated as immediate release layer "IR" and modified release layer "MR". Each drug containing unit is separated by a plug, designated by "Plug" and each plug is separated by a self-breaking layer, designated by "SBL".

As shown in FIGS. 1 through 3, the present invention comprises a core tablet comprising two or more drug containing units 2, designated by "Drug" separated a self-breaking layer 3 designated by "SBL". In one embodiment, as depicted in FIGS. 2 and 3, the core tablet further comprises plugs 4 between the drug 2 and the self-breaking layer 3. The plugs prevent compromise and/or differences in drug release profile of the drug containing units caused by breakage and/or disintegration of the self-breaking layer of the tablet.

The drug containing unit may comprise a single orally administered drug or multiple orally administered drugs. Each drug containing unit may comprise the same amount of drug or drugs. Alternatively, each drug containing unit may contain different amounts of drug or drugs and/or different drugs when more than one drug is being administered.

As shown in FIG. 3, the drug containing unit may comprise more than one drug and/or may exhibit different drug release profiles. In FIG. 3, multiple drug containing layers 2a and 2b of the drug containing unit are designated as "Drug 1" and "Drug 2" and the different drug release layers of the drug containing unit are designated as immediate release layer "IR" and modified release layer "MR". As will be understood by the skilled artisan upon reading this disclosure, additional drugs may be included as well as alternative release layers. For example, when the core tablet is comprised of a single drug, the possible drug release mechanisms include immediate release, modified release (all types of release mechanisms except immediate release) or a combination thereof. When the core tablet is comprised of multiple drugs, the possible drug release mechanisms include all drugs exhibiting immediate release, all drugs exhibiting modified release (all types of release mechanisms except immediate release) or some drugs exhibiting immediate release and some drugs exhibiting modified release.

As will be understood by the skilled artisan upon reading this disclosure, core tablets and coated tablets of the present invention may comprise additional drug containing units, self-breaking layers and plugs as well as additional self-breaking layers in between.

Figure 4:
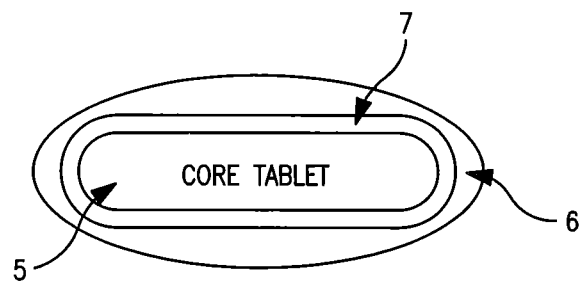
FIG. 4 is a cross-sectional view of an embodiment of a self-breaking tablet of the present invention with a subcoating and a functional coating or film.

As shown in FIG. 4, the core tablet 5 can be coated or compressed with one or more functional coatings or films 6. Further, before coating or compressing the core tablet with a functional coating or film, the core tablet may first be coated with an optional subcoating 7.

In one embodiment, the functional coating is porous so that upon contact with an aqueous media the self-breaking layer swells, breaks and disintegrates.

In an alternative embodiment, where the tablet is coated with a non-porous functional coating, a cut or break is made in the coating of the self-breaking layer of the tablet. Such cuts or breaks can be made following coating of the tablet, for example by laser incision or a cutting device or instrument such as, a blade, rasp, file or the like.

The self-breaking layer of any of the tablet or core tablet embodiments of the present invention may contain a drug or drugs immediately released upon disintegration of this layer in an aqueous media. This drug or drugs may be the same as in the drug or drugs of the drug containing units or different.

Alternatively, or in addition, the self-breaking layer may also contain flavoring agents, sweeteners, effervescent agents, coloring agents and such which improve patient compliance.

Formulations of the present invention can be used with any orally administered drug which can be compressed into tablet layers. Examples include, but are not limited to, alpha-2 adrenergic agents, analgesics, angiotensin-converting enzyme (ACE) inhibitors, antianxiety agents, antiarrhythmics, antibacterials, antibiotics, anticoagulants, anticonvulsants, antidepressants, antidiabetics, antiemetics, antiepileptics, antifungals, antihelminthics, antihistamines, antihyperlipidemics, antihypertensives, antiinfectives, antimalarials, antimicrobials, antimigraine agents, antimuscarinic agents, antineoplastic agents, antiprotozoals, antipsychotics, antispasmodics, antiretroviral agents, antivirals, attention-deficit hyperactivity disorder (ADHD) agents, β-blockers, calcium channel blockers, chemotherapeutic agents, cholinesterase inhibitors, Cox-2 inhibitors, decongestants, diuretics, histamine-2 receptor antagonists, hypnotics, hypoglycemic agents, hypotensive agents, immunosuppresants, lipotropics, neuroleptics, opioid analgesics, peripheral vasodilators/vasoconstrictors, proton pump inhibitors, sedatives, serotonin receptor agonists, sympathomimetics as well as pharmaceutically acceptable salts, solvates, hydrates, stereoisomers (racemates, individual enantiomers or diastereomers, or any combination thereof), or polymorphs thereof, or pharmaceutically acceptable combinations comprising at least one of the foregoing active agents, and the like.

In one embodiment, the self-breaking layer of the tablets of the present invention is prepared by direct compression of suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; magnesium carbonate; magnesium oxide; and other agents such as acacia and alginic acid.

Agents that further facilitate disintegration and/or solubilization such as superdisintegrants are added to this self-breaking layer. Examples include, but are not limited to cross-linked polyvinyl pyrrolidone, sodium starch glycolate, Croscarmellose Sodium, alginic acid, or a salt thereof, such as sodium alginate, microcrystalline cellulose and corn starch.

Tablet binders can also be used in the self-breaking layer of the tablet. Examples include, but are not limited to, acacia, methylcellulose, sodium carboxymethylcellulose, polyvinylpyrrolidone (POVIDONE), hydroxypropyl cellulose, hydroxypropyl methylcellulose, sucrose, starch and ethylcellulose.

Lubricants can also be used in the self-breaking layer of the tablet. Examples include, but are not limited to, magnesium stearates, stearic acid, sodium stearyl fumerate, talc, waxes, oils, silicon dioxide and colloidal silica.

A drug or drugs for immediate release upon contact of the tablet with an aqueous media may also be included in the self-breaking layer.

Alternatively, or in addition, agents that improve patient compliance such as flavoring agents, sweeteners, effervescent agents, coloring agents and such can also be added to the self-breaking layer.

The self-breaking layer or layers of the tablets are formulated, for example, by preparing a powder mixture of the excipients with or without the drug(s), by dry blending or granulating or slugging, adding a lubricant and additional disintegrant and pressing the mixture into tablet layers.

In one embodiment, the drug containing unit of the core tablets and tablets of the present invention comprises an immediate release drug containing layer prepared by direct compression of a mixture of the drug or drugs with a suitable carrier or excipient, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; magnesium carbonate; magnesium oxide; and other agents such as acacia and alginic acid.

Agents that facilitate disintegration and/or solubilization can also be added to the drug containing unit. Examples include, but are not limited to cross-linked polyvinyl pyrrolidone, sodium starch glycolate, croscarmellose sodium, alginic acid, or a salt thereof, such as sodium alginate, microcrystalline cellulose and corn starch.

Tablet binders can be used in the drug containing unit as well and include, but are not limited to, acacia, methylcellulose, sodium carboxymethylcellulose, polyvinylpyrrolidone (POVIDONE), hydroxypropyl cellulose, hydroxypropyl methylcellulose, sucrose, starch and ethylcellulose.

Lubricants can also be used in the drug containing unit and include, but are not limited to, magnesium stearates, stearic acid, sodium stearyl fumerate, talc, waxes, oils, silicon dioxide and colloidal silica.

The immediate release layer of the drug containing unit of the tablets is formulated, for example, by preparing a powder mixture of drug or drugs by dry blending or granulating or slugging, adding a lubricant and disintegrant and pressing the mixture into tablet layers.

A modified release layer or layers or portion or portions of a drug containing unit of the core tablet can be prepared by incorporating release retarding excipients into the above-described formulation for the immediate release drug layer or portion, and either completely omitting or reducing the amount of disintegrants.

Examples of release retarding excipients include, but are not limited to hydrophilic polymers such as hydroxypropylmethylcellulose, hydroxymethylcellulose, hydroxypropylcellulose and hydroxyethylcellulose, and which swell in contact with aqueous liquids, and control release of the drug by diffusion through the swollen polymer network.

Examples of other release retarding excipients include, but are not limited to, waxes such as carnauba wax, bees wax stearic acid and gums such as acacia, acrylic polymers, shellac, zein, polyvinylpyrrolidine including crosslinked polyvinylpyrrolidinone, vinyl acetate copolymers, polyethylene oxides, polyvinyl alcohols, and combinations comprising at least one of the foregoing materials.

The modified release layer or layers of the drug containing unit of the tablets are formulated, for example, by preparing the powder mixture of drug or drugs by dry blending or granulating or slugging, adding a lubricant and release retarding excipients pressing the mixture into tablet layers.

In one embodiment, as depicted in FIG. 1, two or more drug containing units, and a self-breaking layer or layers are then compressed to form a single core tablet of the present invention.

In another embodiment, as depicted in FIGS. 2 and 3, the core tablet further comprises plugs.

The plugs may comprise any biocompatible compound or mixture of compounds. The plugs may be soluble or insoluble, permeable or impermeable, pH dependent or pH independent or any combination thereof depending upon the drug or drugs to be orally administered and/or the release mechanism required. Preferably, the plugs are inert, insoluble and impermeable to drug in the drug containing unit regardless of thickness so that breakage of the core tablet at score in the plug has no impact on drug release. Accordingly, the plug preferably comprises no drug or drug in an amount which does not significantly modify bioequivalence and/or functionality of a functional coating or film on the tablet upon breaking or splitting.

Exemplary biocompatible materials for use in the plugs include, but not limited to, waxes, polymers, gums and other pharmaceutically acceptable excipients either alone or in combination.

Exemplary wax excipients include, but are not limited to, wax and wax-like excipients such as carnauba wax, vegetable wax, fruit wax, microcrystalline wax, bees wax (white or bleached, and yellow), hydrocarbon wax, paraffin wax, cetyl esters wax or a combination comprising at least one of the foregoing waxes. Other suitable wax excipients include, for example, fatty alcohols (such as lauryl, myristyl, stearyl, cetyl or specifically cetostearyl alcohol), hydrogenated vegetable oil, hydrogenated castor oil, fatty acids such as stearic acid, fatty acid esters including fatty acid glycerides (mono-, di-, and tri-glycerides), polyethylene glycol (PEG) having a molecular weight of greater than about 3000 number average molecular weight, $M_n$ (e.g. PEG 3350, PEG 4000, PEG 4600, PEG 6000, and PEG 8000), or a combination comprising at least one of the foregoing.

Exemplary polymer excipients include, for example acrylic polymers, alkylcelluloses including substituted alkylcelluloses, shellac, zein, polyvinylpyrrolidine including crosslinked polyvinylpyrrolidinone, vinyl acetate copolymers, polyethylene oxides, polyvinyl alcohols, and combinations comprising at least one of the foregoing materials.

Suitable acrylic polymers that can be used as a plug include, but are not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, or a combination comprising at least one of the foregoing polymers.

Suitable alkylcelluloses and substituted alkyl celluloses include, but are not limited to, methyl cellulose, ethylcellulose, hydroxy or carboxy substituted alkyl celluloses (e.g., hydroxylpropylcellulose, crosslinked hydroxypropylcellulose, carboxymethylcellulose, crosslinked sodium carboxymethylcellulose), hydroxy substituted alkyl-alkyl celluloses (e.g., hydroxypropylmethylcellulose), or a combination comprising at least one of the foregoing.

Exemplary additional pharmaceutically acceptable excipients for use in the plugs include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, magnesium aluminum silicate (Veegum), and larch arabogalactan); alginates; polyethylene oxide; inorganic calcium salts; silicic acid; and combinations thereof.

Fillers, tablet binders and lubricants, including the aforementioned, can be used in the plugs singly or in combination.

In one embodiment, the plugs of the tablet of the present invention are formulated, for example, by preparing a powder mixture of plug material by dry blending or granulating or slugging, adding a lubricant and pressing into tablet layers.

In this embodiment, two or more drug containing units, plugs and a self-breaking layer or layers are compressed to form a single core tablet of the present invention.

The core tablet can then be coated or compressed with one or more functional coatings or films. By "functional coating or film" it is meant a coating that modifies the release properties of the formulation. Examples of such coatings or films include, but are not limited to, controlled release, delayed release, modified release, enteric coating, pH dependent coatings, pH independent coatings, and any combinations thereof.

The functional coating material can be in the form of a film coating comprising a solution or dispersion or a compressible powder mixture of a hydrophilic or hydrophobic polymer. Solvents used for application of the functional coating include pharmaceutically acceptable solvents, such as water, methanol, ethanol, methylene chloride, and a combination comprising at least one of the foregoing solvents.

Examples of functional coating materials include, but are not limited to, film forming polymers such as acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, an alkylcellulose including methylcellulose or ethylcellulose, a hydroxyalkylcellulose such as hydroxymethylcellulose, hydroxyethylcellulose, hydroxypropylcellulose and hydroxybutylcellulose, a hydroxyalkyl alkylcellulose such as hydroxyethyl methylcellulose and hydroxypropyl methylcellulose, a carboxyalkylcellulose such as carboxymethylcellulose, an alkali metal salt of carboxyalkylcelluloses such as sodium carboxymethylcellulose, a carboxyalkyl alkylcellulose such as carboxymethyl ethylcellulose, a carboxyalkylcellulose ester, a starch, a pectin such as sodium carboxymethylamylopectine, a chitin derivate such as chitosan, a polysaccharide such as alginic acid, alkali metal and ammonium salts thereof, a carrageenan, a galactomannan, traganth, agar-agar, gum arabicum, guar gum and xanthan gum, a polyacrylic acid and the salts thereof, a polyvinylalcohol, a polyvinylpyrrolidone, a copolymer of polyvinylpyrrolidone with vinyl acetate, a polyalkylene oxide such as polyethylene oxide and polypropylene oxide and a copolymer of ethylene oxide and propylene oxide, or a combination comprising at least one of the foregoing.

The functional coating may optionally comprise a plasticizer, an additional film-former, a pore former, or a combination comprising at least one of the foregoing.

In one embodiment, the functional coating is porous so that upon contact with an aqueous media, the self-breaking layer swells, breaks and disintegrates.

In another embodiment, the functional coating is nonporous and an incision or cut is made in the functional coating at the self-breaking layer so that upon contact with an aqueous media, the self-breaking layer swells, breaks and disintegrates.

The formulations of the present invention can optionally further comprise a subcoating or non-functional coating. By "non-functional coating" it is meant a coating that does not significantly modify the release properties of the total formulation, for example, a cosmetic coating or an interlayer coating used to separate a functional coating from other components of the formulation. A non-functional coating can have some impact on the release of the active agent due to the initial dissolution, hydration, perforation of the coating, etc., but is not considered to cause significant deviation in release from the non-subcoated composition.

Examples of subcoating materials include, but are not limited to, film forming polymers like hydroxyalkyl celluloses such as hydroxymethyl cellulose, hydroxyethyl cellulose, hydroxypropyl cellulose and hydroxybutylcellulose, hydroxyalkyl alkylcelluloses such as hydroxyethyl methylcellulose and hydroxypropyl methylcellulose, polyvinylalcohols, polyvinylpyrrolidones, copolymers of polyvinylpyrrolidone with vinyl acetate, and combinations thereof.

Figure 6:
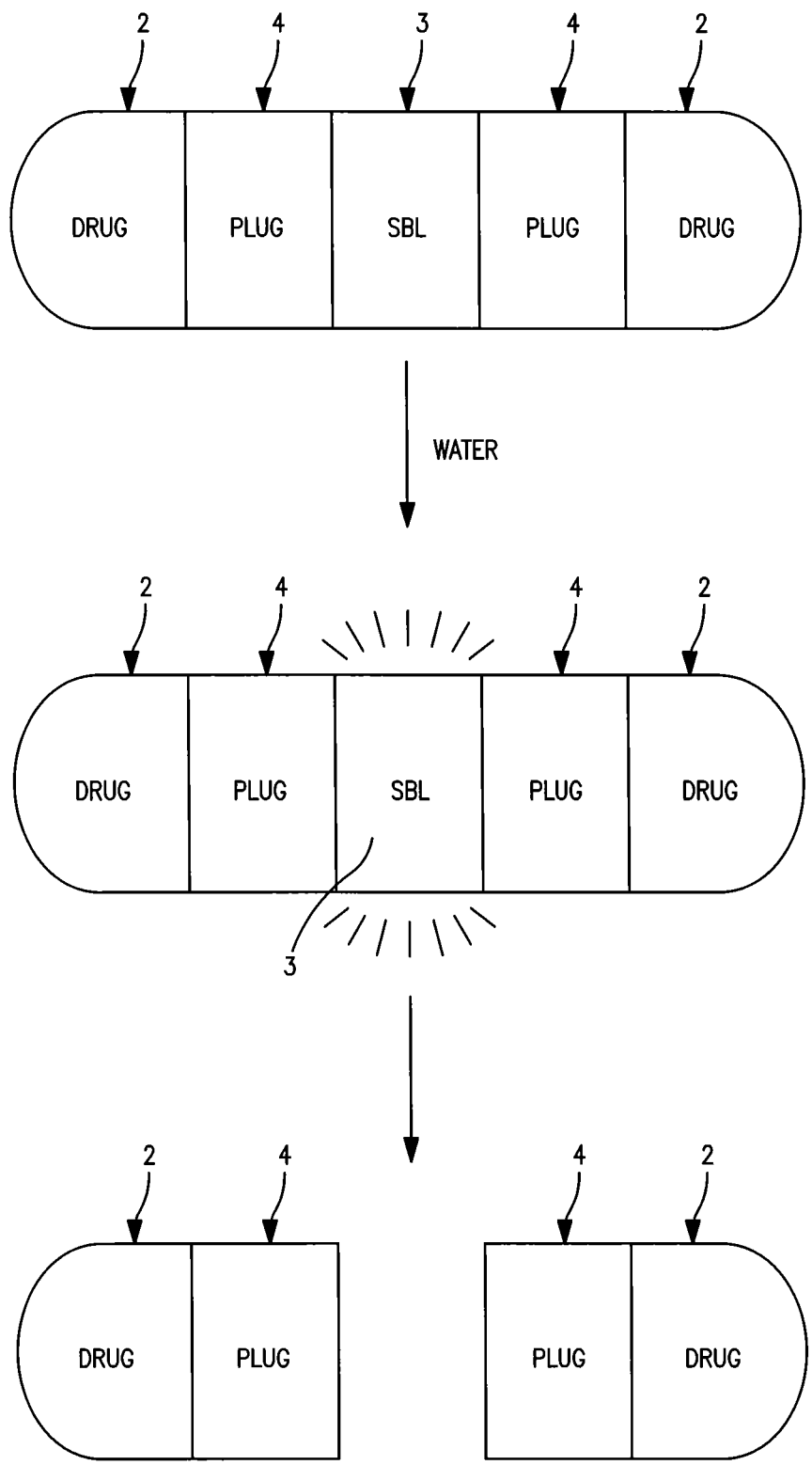
FIG. 6 is a flow diagram depicting breaking of the tablet embodiment of FIG. 2 into two drug containing units upon contact of the tablet with an aqueous media.

Prior to administration to a patient with difficulty swallowing, a tablet of the present invention can be added to a glass of water or juice and mixed for few minutes until the tablet self-breaks into pieces (see FIG. 6).

Figure 5:
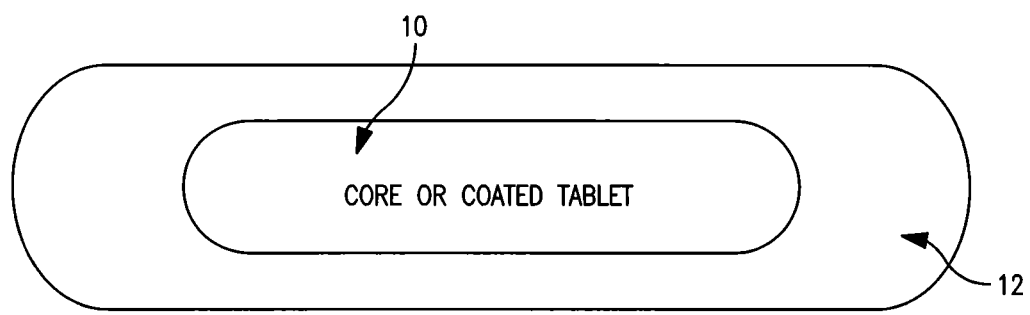
FIG. 5 is a diagram of an embodiment of a capsule of the present invention showing a core or coated tablet of the present invention encapsulated within a capsule.

In another embodiment, as depicted in FIG. 5, one or more of the functionally coated or core tablets 10 of the present invention are encapsulated in a capsule 12. In this embodiment, prior to administration to a patient with difficulty swallowing, the capsule can be opened; the tablet or tablets are removed and added to a glass of water or juice and mixed for few minutes until the tablet or tablets self-break into pieces (see FIG. 6).

Also provided in the present invention are methods for producing these tablet and capsule formulations.

In one embodiment, the method comprises compressing into a core tablet a plurality of drug containing units, each unit separated by a self-breaking layer. In this embodiment, the core tablet can be coated or compressed with one or more functional films or coatings. In this embodiment, the core tablet may be optionally coated with a subcoating prior to coating or compressing with the functional film or coating. In another embodiment, the core tablet is encapsulated in a capsule. In yet another embodiment, the core tablet is coated or compressed with a functional film or coating and then encapsulated into a capsule. In this embodiment, the core tablet may be optionally coated with a subcoating prior to coating or compressing with the functional film or coating.

In another embodiment, the method comprises compressing into a core tablet a plurality of drug containing units, each unit separated by a plug-self-breaking layer-plug. In this embodiment, the core tablet can be coated or compressed with one or more functional films or coatings. In this embodiment, the core tablet may be optionally coated with a subcoating prior to coating or compressing with the functional film or coating. In another embodiment, the core tablet is encapsulated in a capsule. In yet another embodiment, the core tablet is coated or compressed with a functional film or coating and then encapsulated into a capsule. In this embodiment, the core tablet may be optionally coated with a subcoating prior to coating or compressing with the functional film or coating.

The tablets and capsules of the present invention are useful for oral administration of drugs to patients.

Tablets and capsules of the present invention are particularly useful in patients with difficulty in swallowing whole tablets or capsules. For this use, the above described core tablet or coated tablets are added to a glass of water or juice and mixed for few minutes until the tablets self-break into pieces. All broken segments of the core or coated tablet are then administered orally to the patient. For capsule formulation, the core tablet or coated tablet is first removed from its capsule. These tablets are then added to a glass of water or juice and mixed for few minutes until the tablets self-break into pieces. Again, all the broken segments are orally administered to the patient.

The present invention also provides functionally coated tablets comprising a core tablet with one or more self-breaking layers and a functional coating on the core tablet, wherein the tablet breaks itself into two or more pieces at the one or more self-breaking layers of the drug containing core tablet without compromising functionality of the coating. By the phrase "without compromising functionality of the coating" it is meant that the function of the coating remains unchanged upon breaking the tablet at the self-breaking layers. Thus, if the functional coating provides for delayed drug release, timing of release of the drug from the tablet remains the same for the tablet after breaking. Such functionally coated tablets provide a means for efficiently and effectively administering to patients who cannot swallow the entire tablet or capsule.

The following nonlimiting examples are provided to further illustrate the present invention.

EXAMPLES

Example 1

Preparation of Extended Release Multilayer Tablets of Venlafaxine Hydrochloride

The drug containing units contained Venlafaxine hydrochloride (37.5 mg), microcrystalline cellulose (21.5 mg), hypromellose (40.00 mg), and magnesium stearate (3.00 mg).

The plug contained carnauba wax (64 mg), dibasic calcium phosphate (25 mg), stearic acid (10 mg) and magnesium stearate (1 mg).

The self-breaking layer or portion contained microcrystalline cellulose (35 mg), lactose anhydrous (45 mg), hydroxypropyl cellulose (4 mg), croscarmellose sodium (15 mg), and magnesium stearate (1 mg).

The subcoating contained hydroxypropyl methyl cellulose (12.50 mg/tablet), polyethylene glycol 400 (2.50 mg/tablet) and purified water which was removed during processing.

The extended release coating contained Surelease (30.90 mg/tablet), hydroxypropyl methyl cellulose (20.60 mg/tablet) and purified water which was removed during processing.

The drug containing unit was prepared as follows:

Venlafaxine hydrochloride was dry blended with all the ingredients except magnesium stearate and granulated with purified water. The granulate was dried and milled through a suitable screen. Magnesium stearate was screened and then added to the milled granules. The mixture was then blended for about 2 minutes.

The plug was prepared as follows:

Carnauba wax and dicalcium phosphate were mixed in a collette and granulated with a solution of stearic acid in ethyl alcohol. The granulate was then dried, milled and transferred to a blender. Magnesium stearate was screened and then added to the blender. The mixture was then blended for another 2 minutes.

The self-breaking layer was prepared as follows:

All the ingredients except magnesium stearate were dry blended for five minutes in a blender. Magnesium stearate was screened and then added to the blender. The mixture was then blended for another 2 minutes.

The blends were then compressed into a multi-layer core tablet in the following sequence: drug containing unit-plug-self breaking layer-plug-drug containing unit of 100 mg each using a multi-layer tablet press. Core tablets were then subcoated.

The subcoating was prepared by dissolving hydroxypropyl methyl cellulose and polyethylene glycol 400 in purified water and sprayed as a coating solution onto the multi-layer core tablet in a coating pan.

The extended release coating was prepared as follows: In a container purified water was mixed with hydroxypropyl methyl cellulose using mixer until the hydroxypropyl methyl cellulose was completely dissolved. The hydroxypropyl methyl cellulose solution was then added to the Surelease dispersion and mixed for 15 minutes. The resulting dispersion was mixed during the entire coating process. Using the coating pan, the Surelease/hydroxypropyl methyl cellulose dispersion was sprayed onto the subcoated tablets until the required weight gain was achieved.

Example 2

Preparation of Enteric-Coated Multilayer Tablets of Omeprazole

The drug containing unit contained Omeprazole magnesium (22.45 mg/tablet), microcrystalline cellulose (64 mg/tablet), lactose anhydrous (190.55 mg/tablet), hydroxypropyl cellulose (10.00 mg/tablet), croscarmellose sodium (10.00 mg/tablet), and magnesium stearate (3.00 mg/tablet).

The plug contained carnauba wax (128.00 mg/tablet), dibasic calcium phosphate (50.00 mg/tablet), stearic acid (20.00 mg/tablet) and magnesium stearate (2.00 mg/tablet).

The self-breaking layer contained microcrystalline cellulose (35 mg), lactose anhydrous (45 mg), hydroxypropyl cellulose (4 mg), croscarmellose sodium (15 mg), and magnesium stearate (1 mg).

The subcoating contained hydroxypropyl methyl cellulose (15.00 mg/tablet), Polyethylene glycol 400 (3.00 mg/tablet) and purified water which was removed during processing.

The enteric coating contained Eudragit L30D55 (24.32 mg/tablet), triethyl citrate (2.66 mg/tablet), talc (14.62 mg/tablet) and purified water which was removed during processing.

The drug containing unit was prepared as follows:

Omeprazole magnesium was dry blended with all the ingredients except magnesium stearate for five minutes in a blender. Magnesium stearate was screened and then added to the blender. The mixture was then blended for another 2 minutes.

The plug was prepared as follows:

Carnauba wax and dicalcium phosphate were mixed in a collette and granulated with a solution of stearic acid in ethyl alcohol. The granulate was then dried, milled and transferred to a blender. Magnesium stearate was screened and then added to the blender. The mixture was then blended for another 2 minutes.

The self-breaking layer was prepared as follows:

All the ingredients except magnesium stearate were dry blended for five minutes in a blender. Magnesium stearate was screened and then added to the blender. The mixture was then blended for another 2 minutes.

The blends were then compressed into a multi-layer core tablet in the following sequence: drug containing unit (150 mg)-plug (100 mg)-self breaking layer (100 mg)-plug (100 mg)-drug containing unit (150 mg) using a multi-layer tablet press. Core tablets were then subcoated.

The subcoating was prepared by dissolving hydroxypropyl methyl cellulose and polyethylene glycol 400 in purified water and sprayed as a coating solution onto the multi layer core tablet bed in a coating pan.

The enteric coating was prepared by mixing Eudragit L30D55 and triethyl citrate in a container using a mixer. In a separate container purified water was mixed with talc using a mixer until the talc was evenly dispersed in the water. The talc suspension was then added to the Eudragit dispersion and mixed for 15 minutes. The resulting dispersion was mixed during the entire coating process. Using the coating pan, the Eudragit/talc dispersion was sprayed onto the subcoated tablets until the required weight gain was achieved.

A cut or break was made in the coating of the self-breaking layer of the tablet by laser incision.

What is claimed is:

1. A tablet comprising a self-breaking core tablet comprising two or more drug containing units, each unit being separated by an insoluble plug comprising no drug, and each insoluble plug being separated by a self-breaking layer, wherein the self-breaking core tablet is coated or compressed with one or more porous functional films or coatings so that upon contact with an aqueous media, the self-breaking layer disintegrates and the core tablet breaks into separate drug containing units each with insoluble plugs.

2. The tablet of claim 1 wherein the drug containing units comprise a single drug.

3. The tablet of claim 1 wherein the drug containing units comprise two or more drugs.

4. The tablet of claim 1 wherein each drug containing unit comprises one or more different drugs.

5. The tablet of claim 1 wherein the drug containing units comprise two or more different drug release layers.

6. The tablet of claim 1 further comprising a subcoating between the core tablet and the functional film or coating.

7. The tablet of claim 1 wherein the self-breaking layer comprises one or more agents that improve patient compliance.

8. The tablet of claim 1 wherein the self-breaking layer comprises a drug or drugs.

9. The tablet of claim 8 wherein the drug in the self-breaking layer is the same drug as in the drug containing units.

10. The tablet of claim 8 wherein the drug in the self-breaking layer is different from the drug in the drug containing units.

11. A capsule comprising one or more tablets of claim 1 encapsulated in a capsule.

* * * * *